United States Patent [19]  [11] 4,149,001

Sundeen et al.  [45] Apr. 10, 1979

[54] 4,5-DISUBSTITUTED-1-AMINOALKYL CYCLOHEXENES

[75] Inventors: Joseph E. Sundeen, Yardley, Pa.; Frederic P. Hauck, Somerville, N.J.

[73] Assignee: E. R. Squibb & Sons, Inc., Princeton, N.J.

[21] Appl. No.: 934,937

[22] Filed: Aug. 18, 1978

Related U.S. Application Data

[62] Division of Ser. No. 790,784, Apr. 25, 1977.

[51] Int. Cl.$^2$ .................. C07D 211/22; C07D 211/34
[52] U.S. Cl. ................................. 546/238; 546/194; 546/240; 546/275; 260/326.4; 546/326.43; 260/239 B; 260/239 BF; 260/244; 424/244; 424/267; 424/274; 260/326.5 R
[58] Field of Search ....................... 260/293.65, 293.81, 260/293.82, 326.4, 326.43, 326.5 R, 239 B, 239 BF

[56] References Cited
U.S. PATENT DOCUMENTS

| | | | |
|---|---|---|---|
| 3,751,420 | 8/1973 | Hauck et al. | 260/239 B |
| 3,894,031 | 7/1975 | Hauck et al. | 260/326.5 R |
| 3,936,645 | 2/1976 | Hauck et al. | 260/326.5 R |
| 4,033,971 | 7/1977 | Hauck et al. | 260/293.65 |

*Primary Examiner*—Natalie Trousof
*Assistant Examiner*—Robert T. Bond
*Attorney, Agent, or Firm*—Lawrence S. Levinson; Merle J. Smith; Stephen B. Davis

[57] ABSTRACT

Compounds of the formula

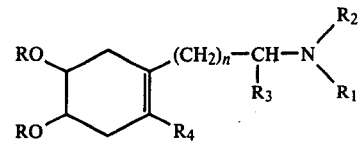

wherein R is hydrogen,

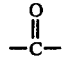

lower alkyl,

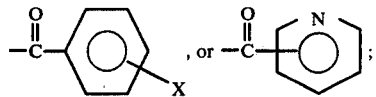

$R_1$ and $R_2$ are independently selected from hydrogen, lower alkyl, and cycloalkyl or $R_1$ and $R_2$ taken together with the nitrogen atom to which they are attached from a ring of the formula

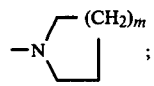

n is 0 or an integer from 1 to 3; m is an integer from 1 to 3; $R_3$ and $R_4$ are independently selected from hydrogen and lower alkyl; X is hydrogen, halogen, lower alkyl, lower alkoxy, or nitro; and their salts; are disclosed. These compounds possess useful antiinflammatory properties.

9 Claims, No Drawings

4,5-DISUBSTITUTED-1-AMINOALKYL CYCLOHEXENES

This is a division of pending application Ser. No. 790,784, filed Apr. 25, 1977.

BACKGROUND OF THE INVENTION 4,5,6,7Tetrahydro-indan which can be substituted at the 5 and 6-positions by acyloxy groups and on the other ring by an amino, substituted amino, heterocyclic, alkyleneamino, alkylene (substituted amino), or alkyleneheterocyclic are disclosed as possessing analgetic muscle relaxant activity in U.S. Pat. No. 3,751,420 of Hauck et al.

SUMMARY OF THE INVENTION

This invention is directed to new compounds and their pharmaceutically acceptable acid addition salts of the formula

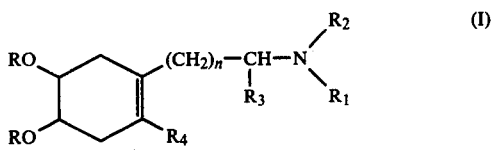

R is hydrogen,

lower alkyl,

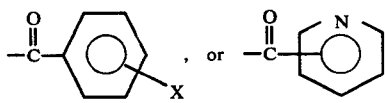

wherein X is hydrogen, halogen, lower alkyl, lower alkoxy or nitro.

$R_1$ and $R_2$ are independently selected from hydrogen, lower alkyl, and cycloalkyl or $R_1$ and $R_2$ taken together with nitrogen atom form a ring of the formula

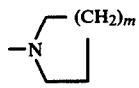

wherein m is 1, 2, or 3.

$R_3$ and $R_4$ are independently selected from hydrogen and lower alkyl.

n is zero or an integer from 1 to 3.

DETAILED DESCRIPTION

The term "lower alkyl" is meant to include straight or branched chain hydrocarbon groups of 1 to 4 carbons, i.e., methyl, ethyl, n-propyl, t-butyl. The term "lower alkoxy" includes such alkyl groups attached to an oxygen atom.

The term "cycloalkyl" is meant to include a saturated carbocyclic group of 3 to 7 carbons, preferably 5 to 7 carbons, i.e., cyclopropyl, cyclobutyl, cyclopentyl, cyclohexyl, and cycloheptyl.

The term "halogen" is meant to include the four common members of this group, i.e, chloro, bromo, fluoro, and iodo, with chloro and bromo being preferred.

The compounds of formula I exist as geometric isomers and can be obtained with the -OR substituents in either the cis or trans configuration depending upon the reaction conditions employed. The compounds of formula I are additionally optically active since they contain one or two asymmetric centers. One center is present in the cyclohexene ring while the other is present in the sidechain when $R_3$ is alkyl. Thus, it is possible to obtain either the cis or trans compounds of formula I as a mixture of optically active isomers, a partially resolved compound (when $R_3$ is alkyl), or a completely resolved isomer. All of these stereoisomers are within the scope of this invention.

The cis diols of formula I (i.e. R is hydrogen) are prepared by reacting a diene of the formula

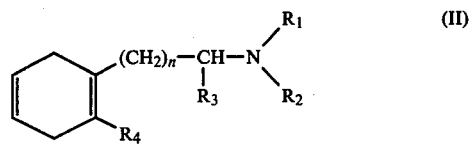

with silver acetate and iodine in the presence of moist acetic acid.

Treatment of the above prepared cis diol in the form of its hydrochloride salt with an acid chloride of the formula

wherein $R_5$ is lower alkyl,

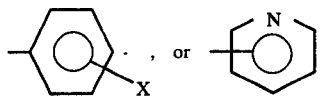

in the presence of trifluoroacetic acid yields the cis ester compounds of formula I.

Also, the cis ester compounds of formula I wherein both $R_1$ and $R_2$ are not hydrogen can be prepared by reacting the cis diol in the form of the free base with an anhydride of the formula

in the presence of pyridine.

The dienes starting materials of formula II are prepared by the Birch reduction of the compound of the formula

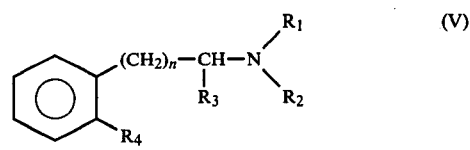

as taught in U.S. Pat. No. 3,936,465 of Hauck et al.

The trans diacetate esters of formula I (i.e., R is

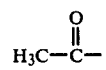

are prepared by reacting a diene of formula II with silver acetate and iodine in the presence of dry acetic acid (Prevost reaction) as taught by Hauck et al. in U.S. Pat. No. 3,894,031 at col. 14.

The resulting trans diacetate ester can then be treated with base such as aqueous sodium hydroxide solution to yield the trans diol of formula I (i.e. R is hydrogen).

Treatment of the above prepared trans diol of formula I with the acid chloride of formula III or the anhydride of formula IV according to the procedures set forth above yields the other trans esters of formula I.

The compounds of formula I can be isolated in the form of a pharmaceutically acceptable acid addition salt. Acids useful for preparing these salts include hydrohalic acids (e.g. hydrochloric and hydrobromic acid), sulfuric acid, nitric acid, and phosphoric acid, and organic acids such as 4-methylbenzenesulfonic acid, acetic acid, oxalic acid, maleic acid, fumaric acid, tartaric acid, citric acid, benzoic acid, 2-acetoxybenzoic acid, salicyclic acid, succinic acid, and methanesulfonic acid.

Preferred compounds of this invention are those of formula I wherein $R_1$ and $R_2$ are independently selected from hydrogen, methyl, and ethyl or $R_1$ and $R_2$ taken together with the N-atom to which they are attached form

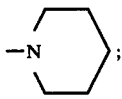

$R_3$ is hydrogen, methyl or ethyl; $R_4$ is hydrogen; and R is hydrogen,

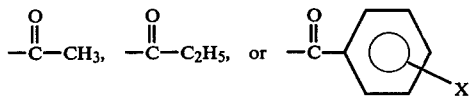

wherein X is hydrogen, Cl, Br, methyl, methoxy, or nitro.

Most preferred are the compounds of formula I in the cis isomeric configuration wherein R is hydrogen or

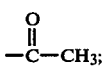

$R_1$ and $R_2$ are independently selected from hydrogen and methyl or $R_1$ and $R_2$ taken together with the N-atom to which they are attached form

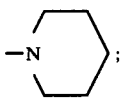

$R_3$ is hydrogen or methyl; and n is 1.

The compounds of formula I and their pharmaceutically acceptable acid addition salts are useful in treating inflammation in mammalian species, e.g. rats, dogs, cats, monkeys, etc. Joint tenderness and stiffness (in conditions such as rheumatoid arthritis) are relieved by the above described compounds.

The compound or mixture of compounds of formula I can be used as antiinflammatory agents according to accepted pharmaceutical practice in oral dosage forms such as tablets, capsules, elixirs, or powders, or in an injectable form in a sterile aqueous vehicle prepared according to conventional pharmaceutical practice. The compounds of this invention may be administered in amounts ranging from about 1 mg./kg./day to about 30 mg./kg./day, preferably from about 3 mg./kg./day to about 15 mg./kg./day. A preferred unit dose for use in treating a 70 kg. mammal would contain from 210 mg. to about 1,050 mg. of active ingredient.

The following examples are illustrative of the invention and represent preferred embodiments. Other modifications may be readily produced by suitable variations of the reactants. All temperatures are in the centigrade scale.

EXAMPLE 1 dl-cis-4-(2-Aminoethyl)-4-cyclohexene-1,2-diol, acetate salt (1:1)

(a) Dihydrophenethylamine

A solution of 50 g. (0.41 moles) of phenethylamine in 1.5 l. of ammonia is treated with 22 g. (3.2 moles) of lithium followed by 350 ml. of absolute ethanol. The reaction solution is evaporated, the residue is taken up in water, and then extracted with ether to yield 50 g. of crude dihydrophenethylamine.

(b) dl-cis-4-(2--Aminoethyl)-4-cyclohexene-1,2-diol, acetate salt (1:1)

25 g. of dihydrophenethylamine (0.2 moles) is dissolved in 1.5 l. of acetic acid and 30 ml. of water. 66 g. (0.4 moles) of silver acetate and then 51 g. (0.4 g atom) of iodine are added to the solution. After stirring for one hour, the mixture is heated under nitrogen for 1.5 hours at 95°, cooled, filtered, and evaporated to an oil. This oil is taken up in methanol and made strongly basic with 10% NaOH. After standing for 4 hours the methanol is removed under reduced pressure and standing gives crystals of sodium acetate. The filtrate is extracted with chloroform and then n-butanol. Evaporation of the n-butanol extracts gives a dark oil. This oil is dissolved in methanol and diluted with acetonitrile to give a first crop of dark oil and then a second crop of lighter oil. After the third dilution, the solution and oil are allowed to stand for two days to form white crystals of the acetate salt product. The mother liquors are evaporated, taken up in acetic acid, stripped, and then slurried with ethyl acetate containing some methanol to yield additional acetate salt product. This material is recrystallized from methanol-acetonitrile, then combined with the material obtained from the butanol extracts and recrystallized from methanol-acetonitrile to yield 8 g. of dl-cis-4-(2-aminoethyl)-4-cyclohexene- 1,2-diol, acetate salt (1:1), m.p. 143–147°.

EXAMPLE 2 dl-cis-4-[2-(Methylamino)ethyl]-4-cyclohexene-1,2-diol, 4-methyl-benzenesulfonate salt (1:1)

46 g. (0.34 moles) of N-methylphenethylamine are reduced by treatment with 16 g. of lithium (2.3 g. atom) in 1.5 l. of ammonia and 250 ml. ethanol according to the procedure of Example 1(a) to yield crude N-methyl-dihydrophenethylamine.

The crude diene is reacted with 110 g. (0.68 moles) silver acetate and 85 g. of iodine (0.68 g. atom) in 1.5 l. of acetic acid and 30 ml. of water at 95° for two hours. The reaction solution is filtered and evaporated to give an oil. This oil is dissolved in excess 10% NaOH and allowed to stand overnight. The solution is extracted with chloroform and then n-butanol. The butanol extracts are dried (MgSO$_4$) and evaporated to an oil. This oil is treated with 4-methylbenzenesulfonic acid in acetonitrile to yield 41 g. of crude salt product.

A 5 g. sample of this crude product is recrystallized twice from methanol-acetonitrile to yield 3 g. of white solid dl-cis-4-[2-(methylamino)ethyl]-4-cyclohexene-1,2-diol, 4-methylbenzenesulfonate salt (1:1); m.p. 144–147°.

EXAMPLE 3 dl-cis-4-[2-(Dimethylamino)ethyl]-4-cyclohexene-1,2-diol-4-methylbenzenesulfonate salt (1:1)

(a) 1-[2-(Dimethylamino)ethyl]-1,4-cyclohexadiene

A solution of 48.5 g. (0.4 mole) of phenylethylamine in 110 g. of 88% formic acid is treated with 100 ml. of 37% formalin and a boiling chip. The solution is heated until bubbling starts and then is heated for 4 hours on a steam bath. 250 ml. of 10% HCl is then added and the mixture is evaporated to an oil. The free base is liberated with sodium hydroxide, extracted into benzene, dried over carbonate and evaporated at 0.2 mm. Hg at 40° to yield 45 g. of colorless dimethylphenethylamine oil.

45 g. (0.3 moles) of the dimethylphenethylamine is reduced by treatment with 16 g. of lithium (2.3 g. atom) in 1.5 l. of ammonia and 250 ml. of ethanol according to the procedure of Example 1(a) to yield crude 1-[2-(dimethylamino)ethyl]-1,4-cyclohexadiene.

(b) dl-cis-4-[2-(Dimethylamino)ethyl]-4-cyclohexene-1,2-diol-4-methylbenzenesulfonate salt (1:1)

The crude diene product from part (a) is reacted with 1.5 l. of acetic acid, 30 ml. of water, 100 g. of silver acetate and 75 g. of iodine according to the procedure of Example 2. The cooled hydrolysis mixture is extracted with ether, chloroform, and n-butanol. The chloroform extract contains the diol product and 40 g. are obtained after drying (Na$_2$SO$_4$) and evaporating.

11 g. (0.05 moles) of cis-4-[2-(dimethylamino)ethyl]-4-cyclohexene-1,2-diol are treated with 4-methylbenzenesulfonic acid in acetonitrile to yield 7.8 g. of dl-cis-4-[2-(dimethylamino)ethyl]-4-cyclohexene-1,2-diol, 4-methylbenzenesulfonate salt (1:1); m.p. 126–128°.

EXAMPLE 4 dl-cis-4-(2-Aminopropyl)-4-cyclohexene-1,2-diol (a) dl-1-(2-Aminopropyl)-1,4-cyclohexadiene 12 g. (0.09 moles) of α-methylphenethylamine is reduced by treatment with 4 g. of lithium in 0.5 l. of ammonia according to procedure of Example 1(a) to yield 1-(2-aminopropyl)-1,4-cyclohexadiene.

(b) dl-cis-4-(2-Aminopropyl)-4-cyclohexene-1,2-diol dl-4-(2-Aminopropyl)-1,4-cyclohexadiene is treated with 500 ml. of acetic acid, 10 ml. of water, 30 g. (0.18 moles) of silver acetate, and 23 g. (0.18 g. atom) of iodine according to the procedure of Example 2. The cooled hydrolysis mixture is extracted with chloroform to give after removal of the chloroform 4 g. of tan solid. Recrystallization from ethyl acetate including treatment with activated charcoal yields 1.4 g. of dl-cis-4-(2-aminopropyl)-4-cyclohexene-1,2-diol; m.p. 102–106°.

EXAMPLE 5 dl-cis-4-(2-Piperidinoethyl)-4-cyclohexene-1,2-diol, hydrochloride salt (1:1)

(a) 1-(2-Piperidinoethyl)-1,4-cyclohexadiene

A solution of 170 g. (2 moles) of piperidine in 1 l. of tolune is heated nearly to reflux. A solution of 185 g. (1 mole) of phenethyl bromide in 250 ml. of toluene is added at a rate fast enough to cause and maintain a vigorous reflux, which, after addition is completed, is maintained by heating and stirring overnight. The mixture is cooled, diluted to 2.5 l. with ether, and extracted with water. The organic layer is dried (potassium carbonate) and evaporated to an orange liquid. Distillation at 95° and 0.2 mm. Hg affords 169 g. of phenethylpiperidine.

A solution of 63 g. (0.33 moles) of phenethylpiperidine in 250 ml. of isopropanol is added to 3 l. of ammonia at −78°. The solution is warmed to reflux (−33°) and 14 g. (2 moles) of lithium is added in portions. The mixture is blue-bronze with a white oily precipitate. This mixture is stirred for one hour and then treated over two hours with 500 ml. of absolute ethanol until colorless. The ammonia is evaporated overnight and the residue is taken up in ether and water with ice cooling. The organic layers are dried twice with potassium carbonate and evaporated at 10 mm. Hg. and 60° to give 61 g. of crude 1-(2-piperidinoethyl)-1,4-cyclohexadiene.

(b) dl-cis-4-(2-Piperidinoethyl)-4-cyclohexene-1,2-diol, hydrochloride salt (1:1)

A solution of 57.8 g. (0.3 moles) of the diene product from part (a) in 2.5 l. of acetic acid and 50 ml. of water is treated with 99 g. (0.6 moles) of silver acetate and then with 77 g. (0.3 moles) of iodine in six portions over 15 minutes under nitrogen. The mixture is stirred and heated at 90–95° for two hours, filtered hot, the solid washed with more acetic acid, and the filtrate evaporated in vacuo to an oil. This oil is taken up in 750 ml. of 95% ethanol and 500 ml. of water, and basified with solid sodium hydroxide. The mixture is heated on the steam cone for twenty minutes and then evaporated to an aqueous suspension. This suspension is extracted with 1 l. of chloroform, dried (potassium carbonate), and evaporated to an oil. This oil is taken up in benzene and chromatographed on 500 g. of Activity III basic alumina. Elution with chloroform and then 5% methanol in chloroform yields 34 g. of product as a slowly crystallizing oil and 10% methanol yields an additional 12 g. of product.

A 10 g. sample of the diol product (from the 10% methanol fraction) is taken up in 200 ml. of ether and treated with an excess of HCl in isopropanol-ether. The gummy ball which forms is washed with ether, triturated with warm dry acetone, and filtered. Recrystallization from isopropanol-acetone-ether yields dl-cis-4-(2-piperidinoethyl)-4-cyclohexene-1,2-diol, hydrochloride (1:1); m.p. 155–156°.

EXAMPLE 6 dl-cis-4-[2-(Methylamino)ethyl]-4-cyclohexene-1,2-diol, diacetate ester, hydrochloride salt (1:1)

3.97 g. (0.01 mole) of cis-4-[2-(methylamino)ethyl]-4-cyclohexene-1,2-diol, 4-methylbenzenesulfonate salt ((1:1) from Example 2 in 15 ml. of trifuoroacetic acid is cooled in ice and treated with 1.6 ml. (0.022 moles) of acetyl chloride. The mixture is stirred for 0.5 hour at 0° and then for one hour at 25°. The solvent is evaporated in vacuo, saturated bicarbonate is added, and the solution is extracted with ether, ethyl acetate, and chloroform. The organic extracts are combined and evaporated to an oil. This oil is taken up in ethyl acetate and treated with HCl in isopropanol to yield the hydrochloride salt product. Two recrystallizations from acetonitrile-ether yields 0.7 g. of dl-cis-4-[(2-methylamino)ethyl]-4-cyclohexene-1,2-diol, diacetate ester, hydrochloride salt (1:1); m.p. 165–168°.

EXAMPLE 7 dl-cis-4-(2-Aminoethyl)-4-cyclohexene-1,2-diol, diacetate ester

The dl-cis-4-(2-aminoethyl)-4-cyclohexene-1,2-diol, acetate salt (1:1) from Example 1 is treated with a solution of hydrogen chloride in trifluoroacetic acid followed by acetyl chloride according to the procedure of Example 6 to yield dl-cis-4-(2-aminoethyl)-4-cyclohexene-1,2-diol, diacetate ester.

EXAMPLE 8 dl-cis-4-(2-Aminopropyl)-4-cyclohexene-1,2-diol, diacetate ester

The dl-cis-4-(2-aminopropyl)-4-cyclohexene-1,2-diol from Example 4 is treated with a solution of hydrogen chloride in trifluoroacetic acid followed by acetyl chloride according to the procedure of Example 6 to yield dl-cis-4-(2-aminopropyl)-4-cyclohexene-1,2-diol, diacetate ester.

EXAMPLE 9 dl-cis-4-[2-Dimethylamino)ethyl]-4-cyclohexene-1,2-diol, diacetate ester, oxalate salt (1:1)

10 g. (0.055 mole) of dl-cis-4-[2-(dimethylamino)ethyl]-4-cyclohexene-1,2-diol from example 3 is dissolved in 200 ml. of acetic anhydride and 200 ml. of pyridine. The mixture is allowed to stand overnight at 25° and is then stripped in vacuo and treated with excess bicarbonate solution. The mixture is extracted with ether, dried (MgSO₄), and co-evaporated with xylene to give 7 g. of oily diacetate.

The diacetate product is dissolved in isopropanol and treated with a solution of oxalic acid in isopropanol. Dilution with isopropyl ether gives a white solid. Recrystallization from ethyl acetate yields 2.2 g. of crystalline dl-cis-4[2-(dimethylamino)ethyl]-4-cyclohexene-1,2-diol, diacetate ester, oxalate salt (1:1); m.p. 109–112°.

EXAMPLE 10 dl-cis-4-(2-Piperidinoethyl)-4-cyclohexene-1,2-diol, diacetate ester, 4-methylbenzenesulfonate salt (1:1)

A solution of 14 g. (0.062 moles) of dl-cis-4-(2-piperidinoethyl)-4-cyclohexene-1,2-diol from Example 5 in 400 ml. of dry pyridine is treated with 200 ml. of acetic anhydride. The mixture is allowed to stand at room temperature overnight and is then evaporated at 30° in vacuo to a thick oil. This oil is taken up in ether and basified with saturated sodium bicarbonate solution until $CO_2$ evolution ceases. The layers are separated and the aqueous layer is reextracted. The organic layers are dried (sodium sulfate), benzene added, and the mixture evaporated to dryness to give 14.7 g. of crude diacetate product.

3.09 g. (0.01 mole) of the diacetate product in 50 ml. of acetonitrile is treated with a solution of 1.9 g. (0.01 mole) of 4-methylbenzenesulfonic acid in 50 ml. of acetonitrile. The mixture is warmed gently and treated with ether until cloudy. After standing overnight, the mixture is filtered to yield 3.5 g. of crude salt product. Recrystallization from acetonitrileether yields 2.8 g. of dl-cis-4-(2-piperidinoethyl)-4-cyclohexene-1,2-diol, diaetate ester, 4-methylbenzenesulfonate salt (1:1); m.p. 152–153°.

EXAMPLES 11–45

Following the procedure of Examples 1 to 5 the diene shown below in Col. I is converted to the cis diol shown in Col. II. The cis diol of Col. II is then reacted with the acid chloride shown in Col. III according to the procedure of Example 6 or alternatively when $R_1$ and $R_2$ are both not hydrogen with the anhydride of Col. IV according to the procedure of Examples 9 and 10 to yield the cis ester shown in Col. V.

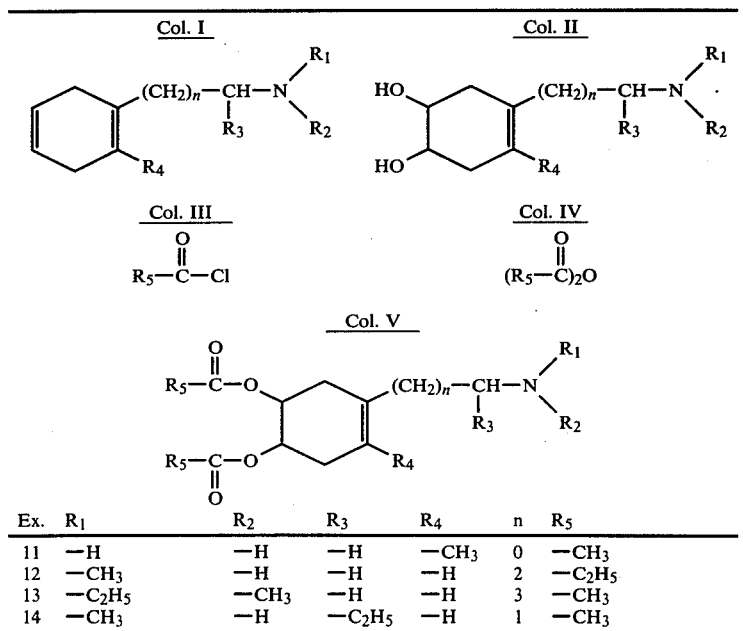

| Ex. | $R_1$ | $R_2$ | $R_3$ | $R_4$ | n | $R_5$ |
|---|---|---|---|---|---|---|
| 11 | —H | —H | —H | —CH₃ | 0 | —CH₃ |
| 12 | —CH₃ | —H | —H | —H | 2 | —C₂H₅ |
| 13 | —C₂H₅ | —CH₃ | —H | —H | 3 | —CH₃ |
| 14 | —CH₃ | —H | —C₂H₅ | —H | 1 | —CH₃ |

-continued
| | | | | | | |
|---|---|---|---|---|---|---|
| 15 | —H | —H | —CH₃ | —C₂H₅ | 1 | —CH₃ |
| 16 | —(CH₂)₂—CH₃ | —H | —H | —H | 2 | —CH₃ |
| 17 | —(CH₂)₃—CH₃ | —H | —H | —CH₃ | 1 | —C₂H₅ |
| 18 | —C(CH₃)₃ | —H | —CH₃ | —H | 0 | —(CH₂)₂—CH₃ |
| 19 | 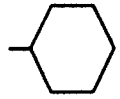 | —H | —H | —CH₃ | 1 | —CH₃ |
| 20 |  | —CH₃ | —H | —H | 1 | —C₂H₅ |
| 21 | 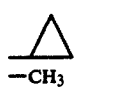 | —H | —CH₃ | —C₂H₅ | 1 | —CH₃ |
| 22 | —CH₃ | —C₂H₅ | —H | —H | 1 | 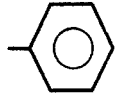 |
| 23 | —H | —H | —H | —C₂H₅ | 2 | 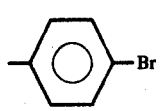 |
| 24 | —CH₃ | —H | —CH₃ | —H | 1 |  |
| 25 | —C₂H₅ | —H | —H | —H | 1 | 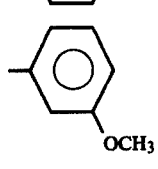 |
| 26 | —CH₃ | —CH₃ | —H | —H | 1 |  |
| 27 | —CH₃ | —H | —CH₃ | —H | 2 | 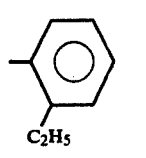 |
| 28 | —CH₃ | —CH₃ | —H | —CH₃ | 3 | 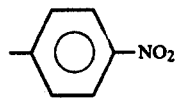 |
| 29 | —CH₃ | —H | —H | —H | 0 | 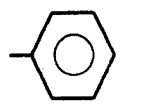 |
| 30 | —H | —H | —CH₃ | —H | 1 | 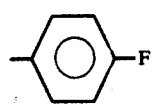 |
| 31 | —CH₃ | —H | —H | —H | 1 | 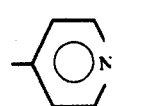 |
| 32 | —H | —H | —CH₃ | —H | 2 | 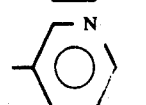 |
| 33 | —CH₃ | —CH₃ | —H | —CH₃ | 1 | 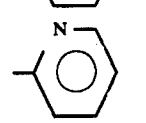 |

| | | | | | |
|---|---|---|---|---|---|
| 34 | —CH$_3$ | —C$_2$H$_5$ | —H | —H | 0 | 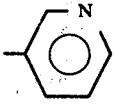 |

| | —N(R$_1$)(R$_2$) | | | | |
|---|---|---|---|---|---|
| 35 | 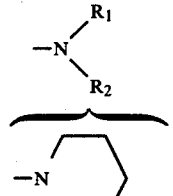 piperidine | —CH$_3$ | —CH$_3$ | 1 | —C$_2$H$_5$ |
| 36 | 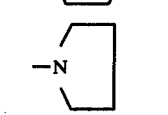 pyrrolidine | —H | —H | 2 | —CH$_3$ |
| 37 |  azepane | —H | —CH$_3$ | 3 | —CH$_3$ |
| 38 | 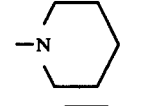 piperidine | —H | —H | 0 | 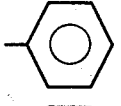 |
| 39 | 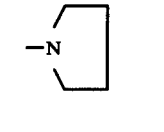 pyrrolidine | —CH$_3$ | —H | 1 | 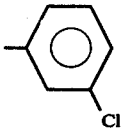 |
| 40 | 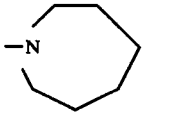 azepane | —H | —H | 2 | 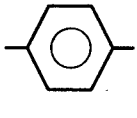 |
| 41 | 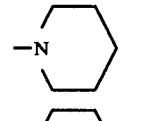 piperidine | —CH$_3$ | —H | 1 | 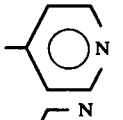 |
| 42 | 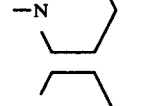 piperidine | —C$_2$H$_5$ | —H | 2 | 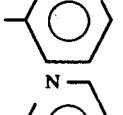 |
| 43 | 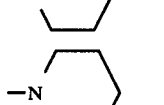 piperidine | —CH$_3$ | —CH$_3$ | 1 | 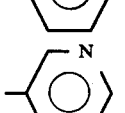 |
| 44 | 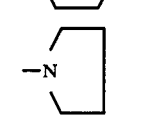 piperidine | —H | —C$_2$H$_5$ | 0 | 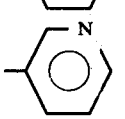 |
| 45 | 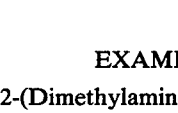 pyrrolidine | —H | —H | 1 | 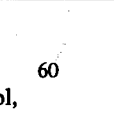 |

EXAMPLE 46 dl-trans-4[2-(Dimethylamino)]-4-cyclohexene-1,2-diol, diacetate eser, hydrochloride salt A solution of 45 g. (0.3 moles) of 1-[2-(dimethylamino)-ethyl]-1,4-cyclohexadiene from Example 3(a) in 1.5 l. of dry glacial acetic acid is treated with 100 g. of silver acetate and 75 g. of iodine. The mixture is stirred until most of the iodine dissolves and is then heated for two hours at 95°. The reaction solution is cooled, filtered and evaporated in vacuo to give an oil. The oil is taken up in ethyl acetate and washed with aqueous sodium bicarbonate solution. The organic phase is dried (MgSO$_4$) and evaporated to an oil. The oil is taken up in ethyl acetate and treated with HCl in isoproanol. The resulting crude solid is removed by filtration and recrystallized from acetonitrile-ether to yield dl-trans-4-[2-(dimethylamino)-ethyl]-4-cyclohexene-1,2-diol, diacetate ester, hydrochloride salt.

EXAMPLE 47 dl-trans-4-[2-(Dimethylamino)ethyl]-4-cyclohexene-1,2-diol, 4-methylbenzenesulfonic acid salt A methanol solution of the dl-trans-4-[2-(dimethylamino)-ethyl]-4-cyclohexene-1,2-diol, diacetate ester, hydrochloride salt from Example 46 is treated with excess 10% sodium hydroxide solution and boiled on a steam cone for 0.5 hours. The methanol is removed in vacuo and the resulting aqueous solution is extracted with chloroform. The extract is dried ($Na_2SO_4$) and evaporated to yield dl-trans-4[2-dimethylamino)ethyl]-4-cyclohexene-1,2-diol as an oily free base. This material is dissolved in acetonitrile and treated with a solution of 4-methylbenzenesulfonic acid. The precipitated solid is recrystallized from acetonitrile to yield dl-trans-4-[2-(dimethylamino)ethyl]-4-cyclohexene-1,2-diol, 4-methylbenzenesulfonic acid salt.

EXAMPLES 48–70

Following the procedure of Example 46 the diene shown in Col. I is converted to the trans diacetate ester shown in Col. II. This trans diacetate ester is then treated according to the procedure of Example 47 to yield the trans diol shown in Col. III. The trans diol of Col. III can then be reacted with trifluoroacetic acid and the acid chloride of Col. IV according to the procedure of Example 6 or when $R_1$ and $R_2$ are both not hydrogen with the anhydride of Col. V according to the procedure of Examples 9 and 10 to yield the trans esters shown in Col. VI.

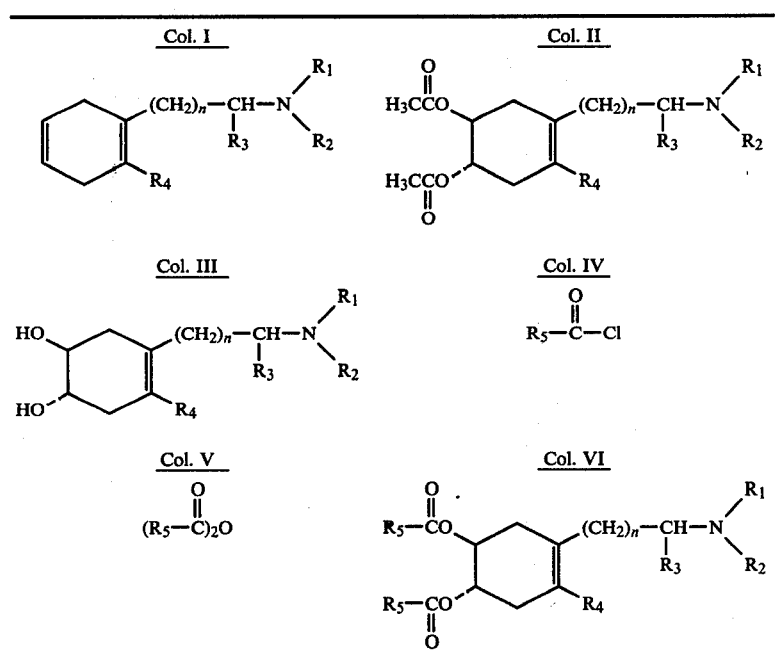

| Ex. | $R_1$ | $R_2$ | $R_3$ | $R_4$ | n | $R_5$ |
|-----|-------|-------|-------|-------|---|-------|
| 48 | —H | —H | —H | —$CH_3$ | 1 | —$C_2H_5$ |
| 49 | —$CH_3$ | —H | —H | —H | 3 | —$C_2H_5$ |
| 50 | —$CH_3$ | —$CH_3$ | —$CH_3$ | —H | 2 | —$(CH_2)_2$—$CH_3$ |
| 51 | —$C_2H_5$ | —H | —H | —H | 0 | —$C_2H_5$ |
| 52 | —$(CH_2)_2CH_3$ | —H | —H | —$C_2H_5$ | 1 | —C₆H₅ (phenyl) |
| 53 | —$C(CH_3)_3$ | —$CH_3$ | —H | —H | 1 | 4-chlorophenyl |
| 54 | cyclohexyl | —H | —$CH_3$ | —H | 1 | 3-bromophenyl |
| 55 | cycloheptyl | —$CH_3$ | —H | —H | 2 | 4-methylphenyl |

-continued

| No | R1 | R2 | R3 | R4 | n | Ar |
|---|---|---|---|---|---|---|
| 56 | cyclohexyl | —H | —CH₃ | —H | 1 | 4-nitrophenyl |
| 57 | —CH₃ | —H | —H | —C₂H₅ | 2 | 3-methoxyphenyl |
| 58 | —CH₃ | —CH₃ | —H | —H | 1 | phenyl |
| 59 | —CH₃ | —H | —H | —H | 1 | 3-pyridyl |
| 60 | —C₂H₅ | —C₂H₅ | —H | —CH₃ | 0 | 3-pyridyl |
| 61 | —H | —H | —CH₃ | —H | 1 | 4-pyridyl |
| 62 | —CH₃ | —H | —H | —H | 3 | 3-pyridyl |

$-N\begin{cases}R_1\\R_2\end{cases}$

| No | —NR₁R₂ | R3 | R4 | n | Ar |
|---|---|---|---|---|---|
| 63 | pyrrolidino | —CH₃ | —H | 0 | —C₂H₅ |
| 64 | piperidino | —H | —H | 1 | —C₂H₅ |
| 65 | hexamethyleneimino | —H | —CH₃ | 3 | phenyl |
| 66 | piperidino | —H | —H | 2 | 4-chlorophenyl |
| 67 | piperidino | —CH₃ | —H | 1 | 4-methoxyphenyl |
| 68 | piperidino | —H | —C₂H₅ | 2 | 3-pyridyl |
| 69 | pyrrolidino | —H | —H | 1 | 4-pyridyl |

| 70 | 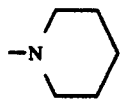 | —CH₃ | —H | 1 | 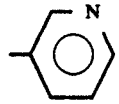 |

What is claimed is:

1. A compound of the formula:

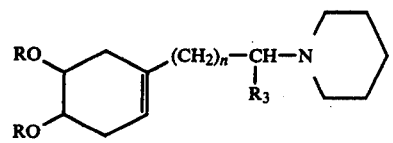

including its sterioisomers wherein R is hydrogen, $$-\overset{O}{\underset{\|}{C}}-$$

lower alkyl, or

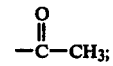

R₃ and R₄ are independently selected from the group consisting of hydrogen and lower alkyl; n is 0 or an integer from 1 to 3; m is an integer from 1 to 3; X is hydrogen, halogen, lower alkyl, lower alkoxy, or nitro; and a pharmaceutically acceptable acid addition salt thereof.

2. The compound of claim 1 of the formula

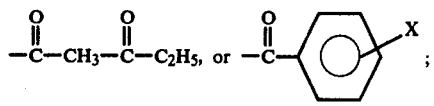

including its sterioisomers wherein R is hydrogen

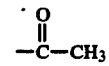

R₃ is hydrogen, methyl, or ethyl; and X is hydrogen, Cl, Br, methyl, methoxy, or nitro.

3. The compound of claim 2 wherein the -OR substituents are in the cis configuration.

4. The compound of claim 3 wherein R is hydrogen or $$-\overset{O}{\underset{\|}{C}}-CH_3;$$

R₃ is hydrogen or methyl; and n is 1.

5. The compound of claim 4 wherein R and R₃ are both hydrogen.

6. The compound of claim 4 wherein R is $$-\overset{O}{\underset{\|}{C}}-CH_3$$

and R₃ is hydrogen.

7. The compound of claim 6, dl-cis-4-(2-piperidinoethyl)-4-cyclohexene-1,2-diol, hydrochloride salt (1:1).

8. The compound of claim 6, dl-cis-4-(2-piperidinoethyl)-4-cyclohexene-1,2-diol, diacetate ester, 4-methylbenzenesulfonate salt (1:1).

9. The compound of claim 2 wherein the -OR substituents are in the trans configuration.

* * * * *

UNITED STATES PATENT AND TRADEMARK OFFICE
CERTIFICATE OF CORRECTION

PATENT NO. : 4,149,001
DATED : April 10, 1979
INVENTOR(S) : Joseph E. Sundeen et al.

It is certified that error appears in the above—identified patent and that said Letters Patent are hereby corrected as shown below:

Col. 7, line 1, "in vacuo" should be underlined or italicized.

Col. 7, line 39, "in vacuo" should be underlined or italicized.

Col. 11, line 61 should read: -- dl-trans-4-[2-(Dimethylamino)-ethyl]-4-cyclohexene-1,2-diol, --.

Col. 12, line 63, "in vacuo" should be underlined or italicized.

*Signed and Sealed this*

*Thirty-first* Day of *July 1979*

[SEAL]

*Attest:*

*Attesting Officer*

LUTRELLE F. PARKER
*Acting Commissioner of Patents and Trademarks*